United States Patent [19]
Cole et al.

[11] Patent Number: 5,282,948
[45] Date of Patent: Feb. 1, 1994

[54] RUGGED O2 MICROSENSOR

[75] Inventors: Barrett E. Cole; Khanh Q. Nguyen, both of Bloomington; Ulrich Bonne, Minnetonka, all of Minn.

[73] Assignee: Gas Research Institute, Chicago, Ill.

[21] Appl. No.: 862,515

[22] Filed: Apr. 2, 1992

[51] Int. Cl.⁵ ............................................. G01N 27/26
[52] U.S. Cl. ...................... 204/421; 204/424; 204/426; 204/428; 204/429
[58] Field of Search ............... 204/421, 424, 425, 426, 204/427, 428, 429

[56] References Cited

U.S. PATENT DOCUMENTS

| | | | |
|---|---|---|---|
| 4,587,105 | 5/1986 | Bonne et al. | 204/425 |
| 4,908,119 | 3/1990 | Saito et al. | 204/426 |

Primary Examiner—John Niebling
Assistant Examiner—Bruce F. Bell
Attorney, Agent, or Firm—Leone & Moffa

[57] ABSTRACT

A rugged $O_2$ microsensor constructed from Si, and Pt, $Si_3N_4$ and $ZrO_2$ thin films which is free standing and isolated from the silicon substrate in combination with a counter electrode and a heater in a bow-tie configuration. The sensor combines an integral heater made from platinum which is deposited on a silicon wafer as a thin film. The thin film heater heats a small yttria-stabilized zirconia sensor that sends a signal proportional to the amount of oxygen in the ambient environment through a counter electrode. The sensor and heater are supported on the silicon wafer by a thin layer of silicon nitride.

10 Claims, 2 Drawing Sheets ns of the Invention

RUGGED O2 MICROSENSOR

This invention relates to a sensor for $O_2$ and more particularly a rugged $O_2$ microsensor configured as a bow-tie and constructed from a suspended thin film of yttria-stabilized zirconia.

BACKGROUND OF THE INVENTION

Accurate assessments of $O_2$ levels are essential for the effective control of fuel firing rate, ambient pressure, temperature and humidity, composition of fuel, stack draft and flow, and combustion air blower speed in combustion systems. With an $O_2$ sensor as provided by this invention, increased efficiency and safety of the combustion system is significantly improved. In contrast to the present invention, conventional $O_2$ sensors whose active sensor area is constructed from $ZrO_2$ suffer from a number of drawbacks:

They utilize large electric heaters with power dissipation from 10 watts to 100 watts. This power is used to heat the sensor to an operating temperature of 800° C.

Mechanical stresses induced by heating and by thermal expansion are large and lead to a short service life, and the voltage drop on the heater (if integral with the sensor) interferes with the measurement of the $O_2$ signal.

The prior art employed many possible ways in which stabilized (cubic) zirconium oxide can serve as an oxygen sensor. The conventional types and electrode active types are well known in the art.

The pumping or cavity type and the two-or three-terminal type, with an active (redox) electrode of Pd, are able to measure oxygen without the need for a reference gas.

In another type, oxygen is pumped into and out of a small cavity (with or without a leak). This makes the fabrication of an absolute oxygen sensor possible without the need for additional metals like Pd.

Prior art solutions do not teach the combination of a bow-tie configuration in a zirconia based oxygen microsensor design wherein the zirconia film is supported by a $Si_3N_4$ layer.

U.S. Pat. No. 4,587,105 to Bonne and Johnson teaches an oxygen sensor built on a silicon chip which has an $SiO_2$ dielectric layer bridging over a depression in the surface of the chip. It does not teach the bow-tie configuration of the present invention.

U.S. Pat. No. 4,839,019 is directed to a limited current-type oxygen sensor comprising an oxygen ion conductive solid state electrolyte, a detection element including a positive electrode, and a negative electrode, and a heater element. The body is formed by a plurality of adjacent zirconium layers of approximately 100 micrometers in thickness.

U.S. Pat. No. 4,595,485 to Takahashi, et al. is directed to a limiting electric current type oxygen sensor comprising a first electrode of a gas-permeable film, a thin solid electrolyte film which is crystallized along one direction to decrease resistance and which has a thickness falling in the range between 0.1 micrometers and 30 micrometers, and a second electrode of gaspermeable film sequentially formed on an electrically insulating substrate. Takahashi, et al. teaches the use of a Pt-film as a heater in a zig-zag pattern. It does not teach the use of $Si_3N_4$ for supporting the $ZrO_2$ film, nor does it show a bow-tie configuration for the sensing device. Other differences are also evident from the figures.

U.S. Pat. No. 4,500,412 to Takahashi, et al. teaches an oxygen sensor with a heater. Takahashi, et al. uses a sensor which has an insulating substrate on which is formed a heater layer for heating the sensor on a part thereof and which is operated above a predetermined temperature. The heater layer is made of a material such as platinum, rhodium, palladium or a mixture thereof. The insulating substrate is made of aluminum, quartz, spinal, magnesia, zirconium or mixtures thereof.

U.S. Pat. No. 4,670,128 to Mase, et al. teaches a device including two electro-chemical cells, one serving as a sensing cell having first and second electrodes, and the other serving as a pumping cell having two electrodes, one of which is exposed to the measurement-gas space. Mase, et al. is directed to a laminar structure and does not use the etching approach of the instant invention.

U.S. Pat. No. 4,639,305 to Shibata, et al. is another example of an electro-chemical sensing element using a laminar structure.

U.S. Pat. No. 4,629,549 to Kojima, et al. teaches an oxygen sensor comprising a plurality of rectangular plates of different materials which uses a built-in oxygen sensor and is intended for use on exhaust pipes.

U.S. Pat. Nos. 4,559,126 and 4,880,519 are other examples of layered designs which have structures radially different from the instant invention.

U.S. Pat. No. 4,571,285 teaches an oxygen sensor for determining the partial pressure of oxygen in a monitor gas environment, including a diffusion housing of zirconium based material having a gas diffusion aperture, an oxygen ion conductive plate of zirconium based material, a pair of electrode layers mounted on opposite sides of the conductive plate, and a ceiling glass material bonding the conductive plate at one side to the housing to provide a diffusion chamber defined by the diffusion housing and the conductive plate.

U.S. Pat. No. 4,900,412 to Kerr, et al., teaches a solid electrolyte oxygen sensor using a heating sub-assembly. The device includes a substantially tubular solid electrolyte body having an elongated board centrally and axially located.

It is therefore the motive of the invention to provide a rugged $O_2$ microsensor configured as a bow-tie and constructed from a suspended thin film of yttria-stabilized zirconia. The invention is useful for industrial and commercial combustion equipment. The invention can be used to sense low levels of excess air to help achieve maximum possible efficiency, safety or flue gas cleanliness.

SUMMARY OF THE INVENTION

The invention provides a rugged $O_2$ microsensor constructed from Si, Pt, $Si_3N_4$ and a $ZrO_2$ film which is free standing and isolated from the silicon substrate in combination with a point-filter electrode in a bow tie configuration.

It is an object of the invention to provide a rugged $O_2$ microsensor.

It is another object of the present invention to sense $O_2$ utilizing $ZrO_2$ as the active sensing material.

It is yet another object of the present invention to sense $O_2$ with a microsensor with an integral heater capable of withstanding heat temperatures of well over 800° C.

It is a further object of the invention to provide an $O_2$ microsensor with a point filter configured as a bow tie.

It is a further object of the invention to provide an O$_2$ sensor with reduced interference from an integral heater.

It is a further object of the invention to provide an improved method of sensing O$_2$ for industrial and commercial combustion equipment.

It is yet another object of the invention to provide an improved O$_2$ sensor that can be used in an automatic combustion system that adjusts to low levels of excess air, and increases efficiency, safety and assures clean flue gas.

It is a further object of the invention to provide a low cost small-volume, low-power O$_2$ sensor suitable for use in small industrial or commercial equipment.

It is yet another object of the invention to provide an O$_2$ sensor made from a suspended thin film of yttria-stabilized zirconium (YSZ) over a silicon substrate pit.

It is an additional object of the invention to provide an O$_2$ sensor which allows the fabrication of combustion equipment that does not need passive excess air controls as, for example, flue baffles or draft hoods.

Other objects, features and advantages of the present invention will become apparent to those skilled in the art through the Description of the Preferred Embodiment, Claims, and drawings herein wherein like numerals refer to like elements.

DESCRIPTION OF THE PREFERRED EMBODIMENT

The oxygen sensor of the invention is intended for use in medium and small size, for example, 50-5000 kBtu/hr or 20 to 2000 kW input combustion systems. The invention utilizes an integral heater sensor approach. The O$_2$ sensor of the invention is based on the fabrication of a heated film of zirconium oxide using an integral platinum heater deposited on a sensor substrate. The integral heater combined with the excellent thermal isolation of the microsensor of the invention eliminates the need for an external means to heat the zirconium oxide to the required 800° C.

Figure 1:
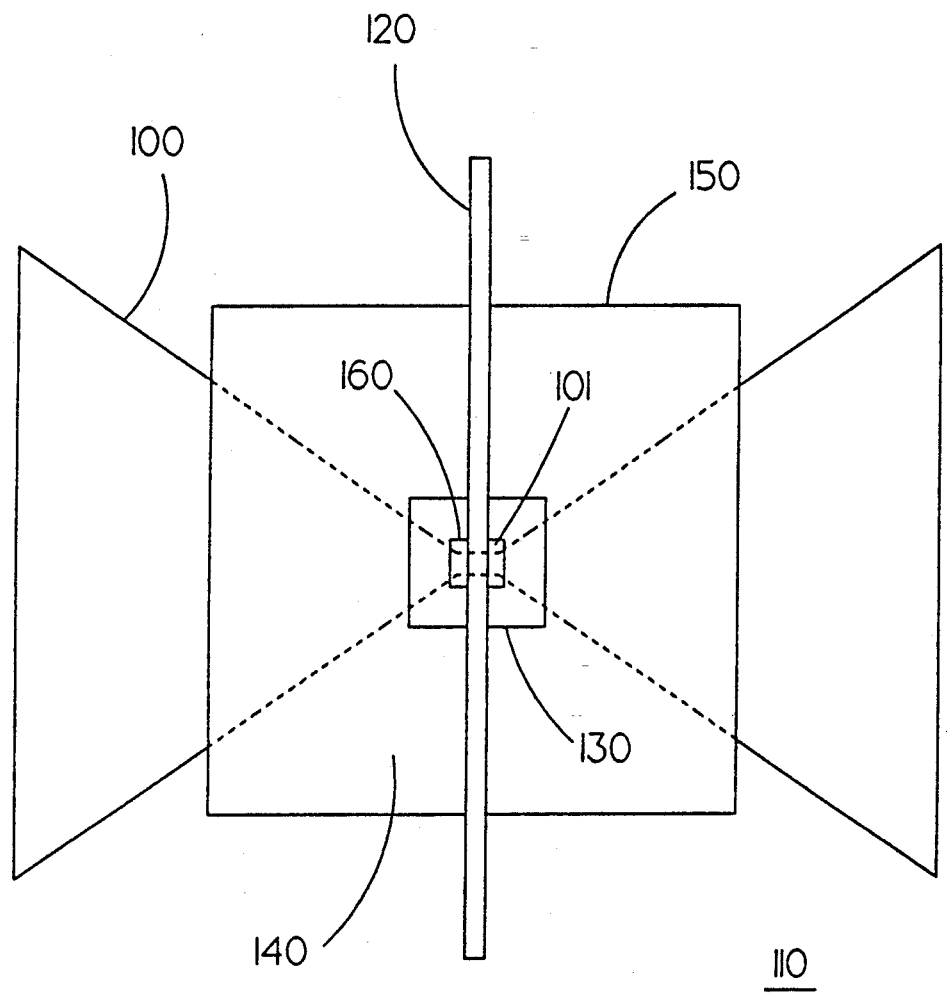
FIG. 1 shows a top down view of the rugged O$_2$ sensor of the invention.

FIG. 1 shows a top view of the sensor chip 10 (FIG. 2) used to manufacture the sensor of this invention. FIG. 1 shows a bow-tie platinum electrode 100 which necks to a small area creating a heater 101 in the center of the membrane 150. The platinum thin film is formed on a silicon substrate 110 in FIG. 1. A silicon nitride (Si$_3$N$_4$) layer 140 is shown surrounding the yttria-stabilized zirconia (YSZ) sensor. The substrate 110 has a pit 152 etched in silicon substrate 110 to form a membrane. A hole 160 is etched in the Si$_3$N$_4$ layer 140 exposing the YSZ sensor 130. A counter electrode 120 is formed transversely to the heater 101. The YSZ sensor 130 is juxtaposed between the counter electrode 120 and the thin film platinum heater 101. A portion of the YSZ sensor 130 is embedded in the Si$_3$N$_4$ layer 140. The platinum counter electrode 120 forms the opposing contact to the YSZ sensor 130.

Figure 2:
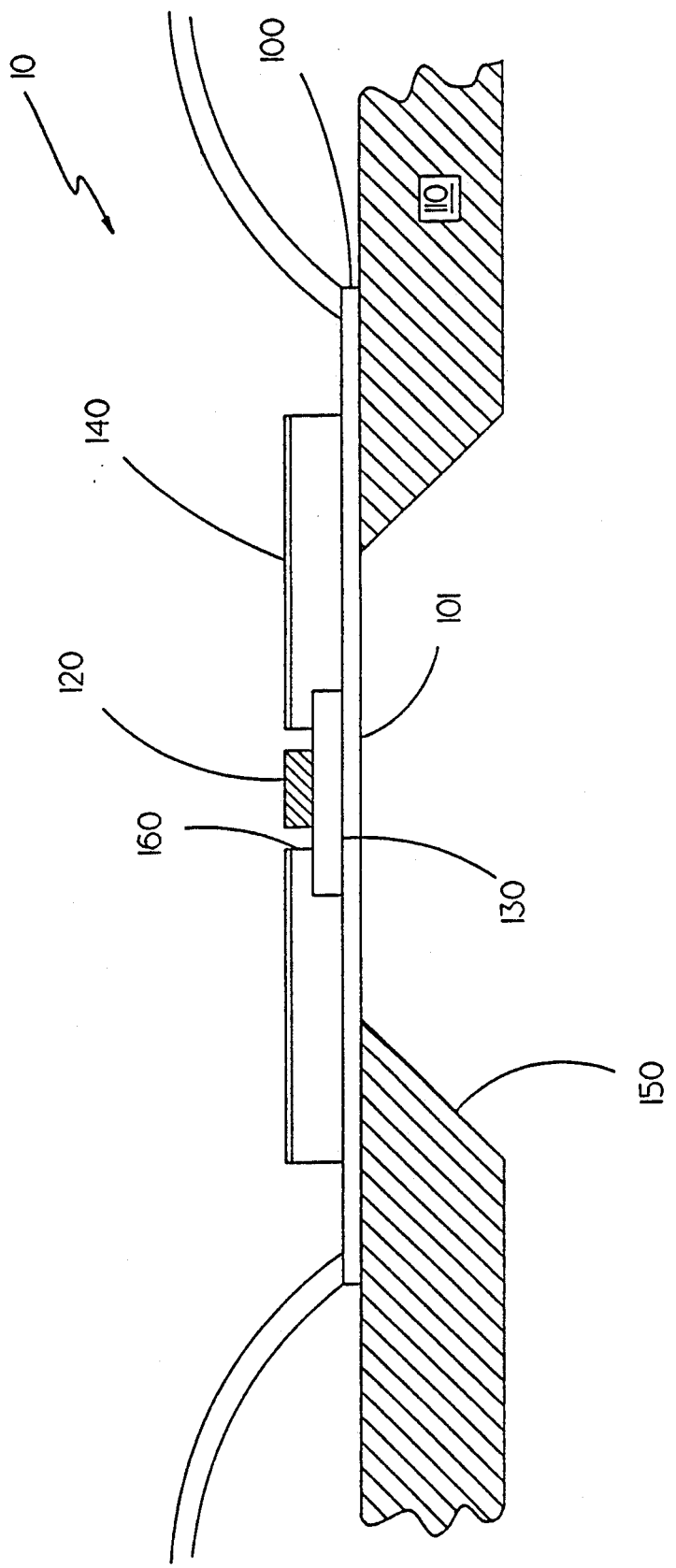
FIG. 2 shows a cross section through A of FIG. 1 showing the layers of the thin film oxygen sensor of the invention.

FIG. 2 shows a cross section of the sensor of FIG. 1. In FIG. 2 the YSZ sensor 130 is shown in the center of the chip 10 located below the counter electrode 120 which makes intimate contact with the YSZ sensor 130. The YSZ sensor 130 is thermally coupled to the platinum thin film heater 101 and, thus, receives thermal energy from the thin film heater. The silicon nitride layer 140 is shown holding the YSZ sensor 130 in position over the platinum heater 101. The silicon wafer 110 is shown with the etched pit 150 beneath the intersection of the counter electrode 120 with the platinum heater 101.

The invention utilizes microstructure fabrication techniques. The process of creating the O$_2$ microsensor utilizes a Pt bow-tie heater 100, 101 constructed from a thin film. The YSZ sensor 130 is also advantageously constructed via thin film deposition. The silicon nitride layer 140 is advantageously constructed to provide structural support, stress control and thermal isolation. The process of constructing the sensor enables the YSZ to be exposed from the two sides of the substrate. This process enables the fabrication of either differential or absolute sensors.

Now that the structure of the sensor has been described the theory and operation of the thin film microsensor will be discussed. The method of the invention exploits the electrochemical potential generated between two regions of the YSZ film maintained at equal temperature. The unique thermal isolation of the thin-film microstructure of the invention permits the maintenance of well-controlled temperatures in the structure.

The invention provides significant advantages over the prior art. The sensor involves fewer fabrication steps and thus is less expensive to make. The sensor of the present invention can also be manufactured with increased strength because it does not require the formation of a YSZ membrane with exposure from both the front of the device and the back of the device simultaneously.

The sensor apparatus of the invention advantageously uses a DC drive mechanism. A prototype of the sensor has been developed and tested by Honeywell Inc. of Minneapolis, Minnesota. Testing of the sensor prototype indicated that the sensor had response times of less than one second. In one example, the sensor proved sensitive to oxygen levels ranging from 100 percent O$_2$ to less than 1 percent O$_2$ with corresponding output signal changes of up to 70 mV. The characteristics of the sensor did not change over many months of periodic testing. The prototype sensor was also found to be insensitive to changes in the fluid flow.

The method of manufacturing the O$_2$ sensor of the invention will now be discussed. Ion beam sputtering may advantageously be employed for depositing the YSZ portion of the sensor onto a wafer. Ion beam sputtering for various materials is well known and consists of depositing a film on a substrate with material that has been sputtered off a target by an energetic beam of inert gas ions, typically argon or xenon. The ions are created in a gun that contains a plasma discharge to ionize the feed gas and a grid extraction system to focus and accelerate the ions. The material sputtered from the target has energies of 5-10 eV. It is this energy, which is much higher than thermal energies, that gives sputtering and, in particular ion beam sputtering, advantages over thermal deposition processes such as electron beam deposition, such as the ability to produce denser films that have excellent adhesion to the substrate.

During deposition the vacuum system is typically at pressures of $2-3 \times 10^{-4}$ Torr, and the plasma is well confined to the ion gun target region of the system. This affords added flexibility in the deposition process as the substrate region of the system can be controlled independently of the deposition source. This is one particular advantage that ion beam sputtering has over most conventional sputter deposition processes.

During the fabrication of the differential $O_2$ sensor of the invention, the heater element is kept as flat as possible and thus avoids the steps generated by other patterned films. In a preferred embodiment of the invention the heater is the first material deposited directly onto the pretreated Si wafer. Heater film thickness of 1000 Angstrom provides heater resistance of approximately 10 ohms.

The second film to be deposited is a YSZ film, which is subsequently patterned onto the existing heater to form the sensing material. Experimental data has shown that the deposited YSZ film is a highly compressively stressed material. If too much of it is used in the sensor the stresses become so great that when the membrane is formed as the final process step, the membrane frequently ruptures. This problem has been solved by using as small an amount of YSZ as possible by locating a small patch of roughly 300 microns of YSZ in the center of the structure. Since yttria-stabilized zirconium also has great resistance to most chemical etches, it cannot be patterned by a selective chemical etch. In addition, the fact that thin Pt electrodes lie below the YSZ film precludes the use of a milling procedure for patterning the YSZ film for fear of also milling through the heater. Advantage can be taken of the fact that ion beam sputter deposition is a relatively low-temperature process to pattern the YSZ film by lift-off techniques. In such a process, photoresist is deposited everywhere except where the YSZ is to remain. The YSZ is deposited on the entire wafer, and when the photoresist is removed, all YSZ that lies on it is removed. A second advantage of this procedure is that it provides a gradual slope onto which the counter electrode can be deposited. The gradual slope ensures that there is continuity in the counter electrode from the edge of the membrane up to the YSZ plateau.

The final process step is to deposit silicon nitride on the sensor to form a bridge from the YSZ material to the edge of the membrane that will be formed after etching. The silicon nitride serves as a structural member. About 1 micron of silicon nitride helps to relieve the YSZ compressive stress. A final dry plasma etch process is used to cut contacts down through the silicon nitride to the pads that connect to the Pt heater and to similar pads that connect to the counter electrode. In an alternate embodiment of the invention the last two processes have been reversed and the counter electrode has been deposited over the top of the silicon nitride film and exposed YSZ film.

The final step in the processing is to mount the wafer in an etch fixture which protects the device side of the wafer while exposing the back side of the wafer to an isopropyl alcohol-KOH mixture that etches the Si wafer along selected etch planes to produce a pyramid-shaped hole. The etch terminates at the bottom of the stack where the Pt electrode was first deposited.

In one prototype sensor, heaters were deposited and tested to temperatures in excess of 800° C. to demonstrate that high temperatures could be achieved. Initial lifetime measurements on these heaters suggested that temperatures could be sustained for reasonable anticipated device life, especially if operated in a low duty cycle mode. For example, one heater survived 2000 hours of 10-Hz temperature cycling. A duty cycle of 1 percent would mean a total of 200,000 hours of sensor life in this case.

Power levels required to achieve these temperatures were determined to be less than 100 mW as modeled and as measured by resistive and optical techniques. Power levels were deemed to be compatible with battery-powered heater operation. Dynamic sensor properties such as time constants were also determined and were consistent with previous modeling.

Two variants of the differential sensor were fabricated and tested at Honeywell. The first one required a heater input of 10 volts, while the second one described here only required about 1 volt. The lower heater voltage reduced the interference with the 10–100 mV EMF sensor output. In addition, the purposely reduced size of the second version increased the ruggedness and reliability. Tests showed that the prototype sensors exhibited Nernstian changes in output, corresponding to changes in oxygen concentration.

The shape of the heater 100 was designed to provide a small overlap area with the counter electrode 120 which crosses the heater 101 at a right angle. Between the heater 101 and the narrow 20-micron-wide strip counter electrode 120 is a small YSZ patch. In one example, the heater 101 is only 50 microns wide and the counter electrode 120 is 20 microns wide. As a result the sensing region is no larger than 20 microns square. The YSZ can then advantageously be patterned into a range of small regions allowing for overlap between the YSZ and the $Si_3N_4$ structure. Experimentation has shown that the most robust structures were those with the smallest opening in the YSZ and the largest overlap between the YSZ and silicon nitride films. Larger sensor sizes, even those containing less YSZ and with less film overlap, were more prone to tear the silicon nitride.

Honeywell computed a profile resulting from heating the film by either an electric heater or infrared radiation, via a finite element analysis. An approximate fit to this profile is provided by the expression:

$$T = T_M - 2(T_M - T_O)(R/R_M)^2 30 (T_M - T_O)(R/R_M)^4$$

where $T_M$ = Maximum temperature
$T_O$ = Room temperature
$R$ = Radius or distance from membrane center, and
$R_M$ = Maximum radius or half the side of square membrane To describe the performance of this heated film, the individual heat losses were computed with the following result. To heat the center to 700° C. an input power of 76 mW is needed, of which about 6 mW are dissipated by radiation, 40 mW by conduction to the substrate and 30 mW by conduction to the surrounding air. These predictions turned out to be close to experimental values obtained later.

Stress in films can arise because of film growth phenomena and thermal expansion. The YSZ material is compressively stressed and the $Si_3N_4$ stress can be "tuned" to compensate for the YSZ stress. Membrane distortion increased with increasing film size and increasing YSZ thickness, suggesting that from a physical perspective, smaller structures containing minimal amounts of YSZ were more desirable.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An oxygen sensor apparatus comprising:
   (a) a silicon wafer with an etched opening and a top surface;
   (b) a thin film heating means having a top surface positioned over the opening and having two heating electrodes deposited onto the silicon wafer top surface;
   (c) a yttria-stabilized zirconia oxygen sensor means, including top and bottom surfaces, the bottom surface being in contact with the top surface of the thin film heating means;
   (d) a counter electrode means positioned above the yttria-stabilized zirconia sensor to make electrical contact with the top surface of the yttria-stabilized zirconia sensor; and
   (e) a silicon nitride positioning layer deposited on the top surface of the thin film heater partially covering the top surface of the sensor so as to hold the yttria-stabilized zirconia sensor in place.

2. The oxygen sensor apparatus of claim 1 wherein the thin film heating means means further comprises platinum.

3. The oxygen sensor apparatus of claim 2 wherein the counter electrode means further comprises platinum.

4. The oxygen sensor apparatus of claim 3 wherein the silicon nitride positioning layer comprises a thin film of silicon nitride.

5. The oxygen sensor apparatus of claim 4 wherein the thin film heating means comprises a bow-tie shape wherein the bow-tie shape comprises two bow shapes and a common crossing region wherein the common crossing region of the thin film heating means contacts the sensor means so that only the sensor means in contact with the heating means is heated.

6. The oxygen sensor apparatus of claim 5 wherein the opening is close to rectangular.

7. The oxygen sensor apparatus of claim 1 wherein the counter electrode means further comprises platinum.

8. The oxygen sensor apparatus of claim 1 wherein the silicon nitride positioning layer comprises a thin film of silicon nitride.

9. The oxygen sensor apparatus of claim 1 wherein the thin film heating means comprises a bow-tie shape wherein the bow-tie shape comprises two bow shapes and a common crossing region wherein the common crossing region of the thin film heating means contacts the sensor means so that only the sensor means in contact with the heating means is heated.

10. The oxygen sensor apparatus of claim 1 wherein the opening is close to rectangular.

* * * * *

UNITED STATES PATENT AND TRADEMARK OFFICE
CERTIFICATE OF CORRECTION

PATENT NO. : 5,282,948
DATED : 2-1-94
INVENTOR(S) : Barrett E. Cole, et al

It is certified that error appears in the above-indentified patent and that said Letters Patent is hereby corrected as shown below:

Col. 6, the equation "$T = T_M - 2(T_M-T_0)(R/R_M)^2\ 30\ (T_M-T_0)(R/R_M)^4$" should be

-- $T = T_M - 2(T_M-T_0)(R/R_M)^2 + (T_M-T_0)(R/R_M)^4$ --

Col. 6, line 48, "membrane" should be -- membrane. --

In the Claims

Col. 7, line 30, please delete the second occurrence of the word "means".

Signed and Sealed this

Sixth Day of September, 1994

*Attest:*

BRUCE LEHMAN

*Attesting Officer*   *Commissioner of Patents and Trademarks*